US00PP10771P

United States Patent [19]

Stallard

[11] Patent Number: Plant 10,771

[45] Date of Patent: Feb. 2, 1999

[54] *CORNUS ALBA ELEGANTISSIMA* NAMED 'STALTOUCH'

[76] Inventor: Don E. Stallard, 1923 Dock Rd., Madison, Ohio 44057

[21] Appl. No.: 938,648

[22] Filed: Sep. 26, 1997

[51] Int. Cl.[6] ..... A01H 5/00

[52] U.S. Cl. ..... Plt./53.2

[58] Field of Search ..... Plt./53.2

*Primary Examiner*—Elizatbeth Kemmerer

[57] ABSTRACT

This invention comprises a new and distinct variegated dogwood. It is a selected sport that occurred naturally from a group planting of *Cornus alba 'Argenteo-marginata'* (C.a. '*Elegantissima*') at my nursery five years ago. I have successfully propagated this sport asexually by cuttings. The small compact growth habit is what characterizes and makes this new selection distinctive.

2 Drawing Sheets

BACKGROUND OF THE INVENTION

*Cornus alba* is a red stemmed shrub used widely for landscaping purposes. It is an introduction from Europe/Asia, thought to have occurred in 1741. (Rehder) A particularly popular variety has variegated leaves. The white margins of the leaves make it distinctive. Variations do occur in the size of the leaves and in the width of the white (or ivory) margin. This may account for the differences in nomenclature. It is known by an assortment of botanical names, as follows:

*Cornus alba 'Elegantissima'*: Hillier Dictionary of Plants.
*Cornus alba 'Argenteo-marginata'*: Rehder & Dirr & Hortus III.
*Cornus alba elegantissima variegata*: Rehder & Hortus III.
*Cornus alba variegata:* Rehder.
*Cornus alba 'Sibirica Variegata'*: Hortus III.

The current usage seems to favor *Cornus alba 'Argenteo-marginata'*. Out of a block of *Cornus alba 'Argenteo-marginata'* (C.A. '*Elegantissima*'), I discovered a plant that was growing a fraction of the height of the balance of the *Cornus alba 'Argenteo-marginata'* plants. I propagated this unique plant to see if it would retain the dwarf characteristics as well as the variegated foliage of the parent plant.

The first sport was propagated as softwood cuttings in Madison, Ohio, in June of 1992, with 90% rooting. These original cuttings become the plants which would serve as the parent stock for early cutting material. Subsequent softwood cuttings have exhibited high rooting success (90–98%) using common practices, under a misting type system. Hardwood cuttings have been used as propagation material with equal success. Ocassionally, a propagated plant will convert to the more aggressive growth of the parent plant. This has occurred less than 1% of the time. These reverted plants are easy to distinguish and cull out because of the greater stem length (internodal dimensions, see Table 1 that follows). Rooting has been successful without any application of rooting hormones. It is believed that any standard practice that is successful with any *Cornus alba* would be successful with this new selection. Plants of this new selection that have rooted and are grown on for five years continue to exhibit the dwarfing characteristics of the original mother plant.

Having grown this new cultivar along side *Cornus alba 'Argenteo-marginata'* for five years, it exhibits the same hardiness, which is Zones 3–7 according to the *USDA Plant Hardiness Zone Map.* All other horticultural characteristics with the exception of those described below are the same as *Cornus alba 'Argenteo-marginata'*.

The uniqueness of this new cultivar is that of a small compact growth habit as compared to its parent plant, *Cornus alba 'Argenteo-marginata'*. It retains the ornamental characteristics of the parent plant, namely the white-edged, variegated foliage that makes *Cornus alba 'Argenteo-marginata'* popular. The characteristics of 'Staltouch' make it particularly suitable for planting against darker plantings, e.g., Taxus, in rock gardens, as surround plants around specimen trees, etc. The plant's distinguishing characteristics are described in detail below.

DETAILED BOTANICAL DESCRIPTION

Figure 1:
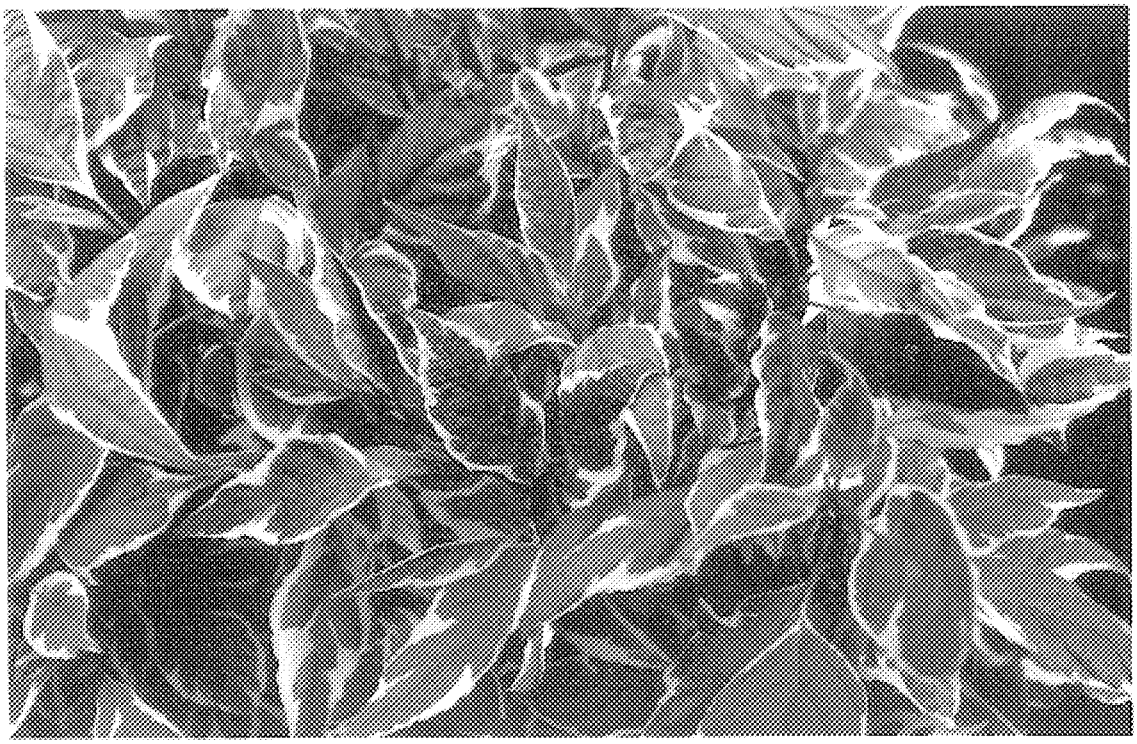
FIG. 1 is a photograph that shows the variegated foliage as comparable to the standard *Cornus alba 'Argenteo-marginata'*. Also, FIG. 1 exhibits the burgundy blush that occurs on the new growth as the plants are leafing out. This burgundy blush becomes more prevalent as part of the fall color.
Figure 2:
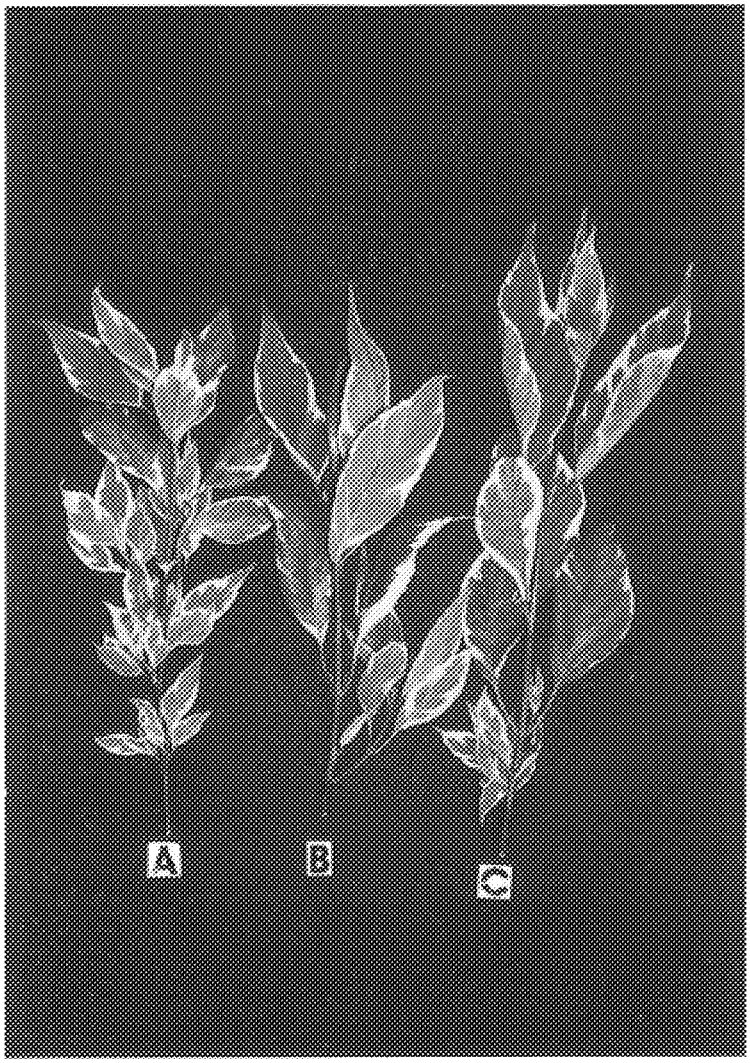
FIG. 2(A)–(C) is a photograph comparing (A.) this new cultivar with (B.) a popular cultivar called 'Ivory Halo'™ (U.S. Plant Pat. No. 8,722) and with (C.) the standard *Cornus alba 'Argenteo-marginata'*. This photograph indicates that shorter internodal length of 'Staltouch' compared to the standard *Cornus alba* 'Argenteo-marginata'.

The following observations were made on a three year old rooted cutting of the mother plant of 'Staltouch'. Morphological characteristics are descried with respect to a standard '*Cornus alba 'Argenteo-marginata'* and *Cornus alba 'Bailhalo'* ('Ivory Halo'™; U.S. Plant Pat. No. 8,722). Color designations are made in accordance with *The Royal Horticultural Society Colour Chart* (*R.H.S.*).

Origin: sport from *Cornus alba* 'Argenteo-marginata'.

Plant:

*Growth habit.*—dwarfed and spreading in comparison to *Cornus alba* 'Argenteo-marginata' and *Cornus alba 'Bailhalo'*.

Spread/height/ratio—.38.1 cm (15 in)/55.9 cm (22 in)= 1.47. This is 199% more spreading than *Cornus alba 'Argenteo-marginata'* (see Table 1).

*Branches.*—multibranched in the absence of pruning; primary branches arising from crown.

*Stolons.*—None.

*Rhizomes.*—None.

Leaves:

*Shape*.—lanceolate and variegated with irregular white margins.

*Size*.—Length: 75.3 mm mean; standard deviation (s.d.) +/−4.9 mm; Coefficient of Variability (C.V.) 6.5%; Confidence-Limits (C.L.) 90%=72.0–78.5 mm. This length is 75.3% of the length of the *Cornus alba 'Argenteo-marginata'* leaves (see Table 2).

Width: 35.5 mm mean; s.d. +/−3.6 mm; C.V. 11.2%; C.L. 90% =33.1–37.9 mm. This width is 82.1% of the length of the *Cornus alba 'Argenteo-marginata'* leaves (see Table 2).

*Color*.—Summer: Grey green (R.H.S. 139C) with irregular white or near white (R.H.S. 157A) variegated edges.

New growth and fall color: Burgundy (R.H.S. 59A) with irregular white to red-purple (R.H.S. 65A) variegated edges.

Stems:

*Shape*.—Erect.

*Size*.—A 300 mm long branch had 14 internodes, no pruning cuts, and 11 naturally occurring secondary branches. Stems are 50% smaller in diameter and more numerous than on *Cornus alba 'Argenteo-marginata'*.

*Internodes*.—mean=21.4 mm; s.d +/−8.8 mm; C.V. 40.8%; C.L. 90%=17.3–25.6 mm. The mean internode length is only 60.8% of that of *Cornus alba 'Argenteo-marginata'*.

*Color*.—Blood-red in winter, usually greener in summer with leaves. Pith is white.

Flowers:

*Appearance*.—sparsely, in cymes, 3.5 to 5 cm across.

*Color*.—yellowish white, typical for *Cornus alba*.

TABLE 1

Height and Spread:

| | HEIGHT | PRUNED | INTERNODE MEAN | HEIGHT/ SPREAD |
|---|---|---|---|---|
| *Cornus alba* '*Argenteo-marginata*' | 26 in. | 3× | 35.5 | 0.74 |
| *Cornus alba* 'Baihalo' | 18 in. | 1× | 28.9 | 1.06 |
| *Cornus alba* 'Staltouch' | 15 in. | 0× | 21.4 | 1.47 |

TABLE 2

Leaf and Stem Dimensions:

| | MILLIMETERS | | | | | | | |
|---|---|---|---|---|---|---|---|---|
| *C. alba* 'Elegantissima' | | | | | | | | |
| Leaf Length | 127 | 119 | 101 | 92 | 99 | 104 | 75 | 83 |
| Leaf Width | 55 | 51 | 41 | 41 | 44 | 40 | 33 | 41 |

TABLE 2-continued

Leaf and Stem Dimensions:

| | | | | | | | | |
|---|---|---|---|---|---|---|---|---|
| Internodes | 21 | 40 | 61 | 57 | 49 | 32 | 25 | 43 |
| *C. alba* 'Bailhalo' | | | | | | | | |
| Leaf Length | 84 | 108 | 98 | 94 | 107 | 117 | 90 | 81 |
| Leaf Width | 39 | 49 | 51 | 52 | 47 | 59 | 47 | 34 |
| Internodes | 47 | 54 | 50 | 38 | 18 | 11 | 12 | 24 |
| C. alba 'Staltouch' | | | | | | | | |
| Leaf Length | 75 | 70 | 84 | 77 | 69 | 72 | 74 | 81 |
| Leaf Width | 35 | 33 | 34 | 36 | 30 | 34 | 39 | 43 |
| Internodes | 36 | 38 | 29 | 18 | 18 | 23 | 23 | 23 |

| | MILLIMETERS | | | | | | MEAN | s.d. +/− | C.V. | C. I. |
|---|---|---|---|---|---|---|---|---|---|---|
| *C. alba* 'Elegantissima' | | | | | | | | | | |
| Leaf Length | | | | | | | 100 | 17.3 | 17.3 | 90 |
| Leaf Width | | | | | | | 43.3 | 6.9 | 15.9 | 90 |
| Internodes | 36 | 33 | 8 | | | | 35.3 | 15.9 | 45.0 | 90 |
| *C. alba* 'Bailhalo' | | | | | | | | | | |
| Leaf Length | | | | | | | 97.4 | 12.6 | 12.9 | 90 |
| Leaf Width | | | | | | | 47.3 | 7.8 | 16.4 | 90 |
| Internodes | 32 | 31 | 25 | 22 | 12 | | 28.9 | 14.7 | 50.9 | 90 |
| *C. alba* 'Staltouch' | | | | | | | | | | |
| Leaf Length | | | | | | | 75.3 | 4.8 | 6.5 | 90 |
| Leaf Width | | | | | | | 35.5 | 3.6 | 11.2 | 90 |
| Internodes | 23 | 19 | 15 | 18 | 12 | 5 | 21.4 | 8.8 | 40.8 | 90 |

mean - in mm
s.d. = standard deviation, in mm
C.V. = coefficient of variability, in %
C.L. = confidence limits, in %

REFERENCES

Manual of Cultivated Plants, Alfred Rehder, Macmillan Co.

The Royal Horticultural Society Colour Chart, Royal Horticultural Society of England USDA Plant Hardiness Zone Map Hillier's Manual of Trees and Shrubs, Yelf Brothers Limited Hortus III, L.H. Bailey Hortorium, Cornell University Photographic Manual of Woody Landscape Plants, Michael Dirr, Stipres Publishing Co.

I claim:

1. A new and distinct cultivar of dogwood (*Cornus alba 'Argenteo-marginata'*) plant designated 'Staltouch', as herein shown as described, characterized by its unique compact growth habit, spreading appearance, and fine dense branching.

* * * * *